(12) United States Patent
Singh et al.

(10) Patent No.: US 6,492,567 B1
(45) Date of Patent: Dec. 10, 2002

(54) **DIHYDROTAGETONE ALCOHOL AND A METHOD FOR PREPARATION THEREOF FROM *TAGETES MINUTA* OIL**

(75) Inventors: Bikram Singh, Palampur (IN); Virendra Prasad Joshi, Palampur (IN); Vijay Kumar Kaul, Palampur (IN)

(73) Assignee: Council or Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/983,544

(22) Filed: Oct. 24, 2001

(51) Int. Cl.$^7$ .............................................. C07C 33/28
(52) U.S. Cl. .................... 568/813; 568/878; 568/909.5
(58) Field of Search .............................. 568/909.5, 878, 568/813

(56) References Cited

U.S. PATENT DOCUMENTS 2,838,576 A  *  6/1958  Normant
4,482,762 A  * 11/1984  Kaiser

* cited by examiner

*Primary Examiner*—Michael L. Shippen
(74) *Attorney, Agent, or Firm*—Nixon & Vanderhye P.C.

(57) ABSTRACT

The present invention provides a novel dihydrotagetone alcohol of the general formula 1, Formula 1

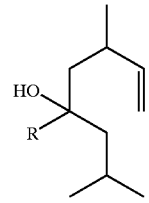

wherein R is an alkyl or aryl group and a process for preparation thereof.

5 Claims, 13 Drawing Sheets

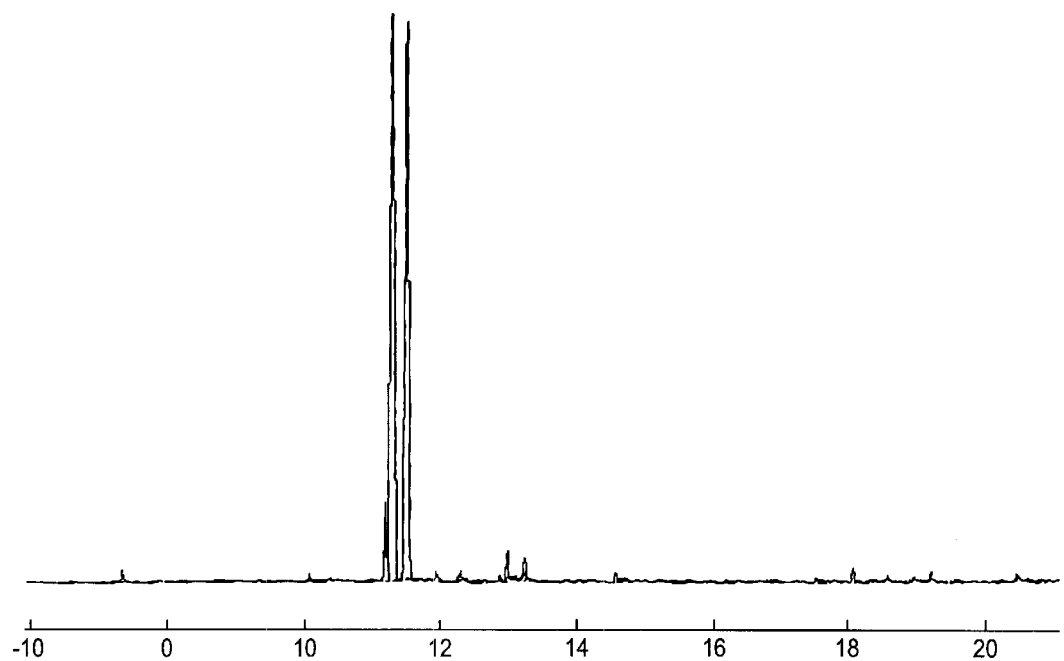
Fig. 1  Gas Chromatograme of Tagetes minuta oil
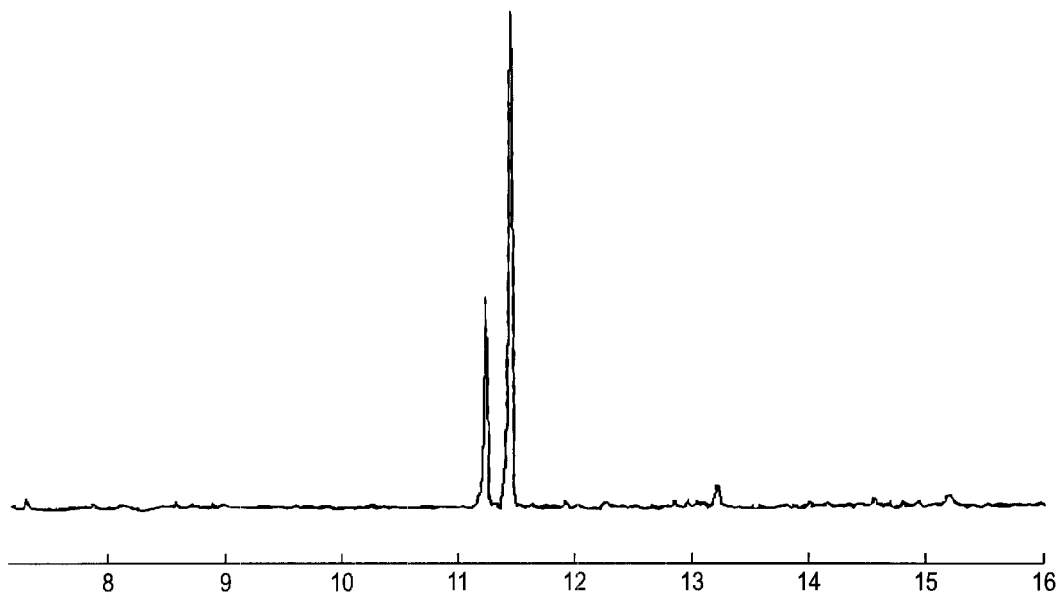
Fig. 2  Gas Chromatograme of 3,7-dimethyl, 5-one, 1-octene rich fraction

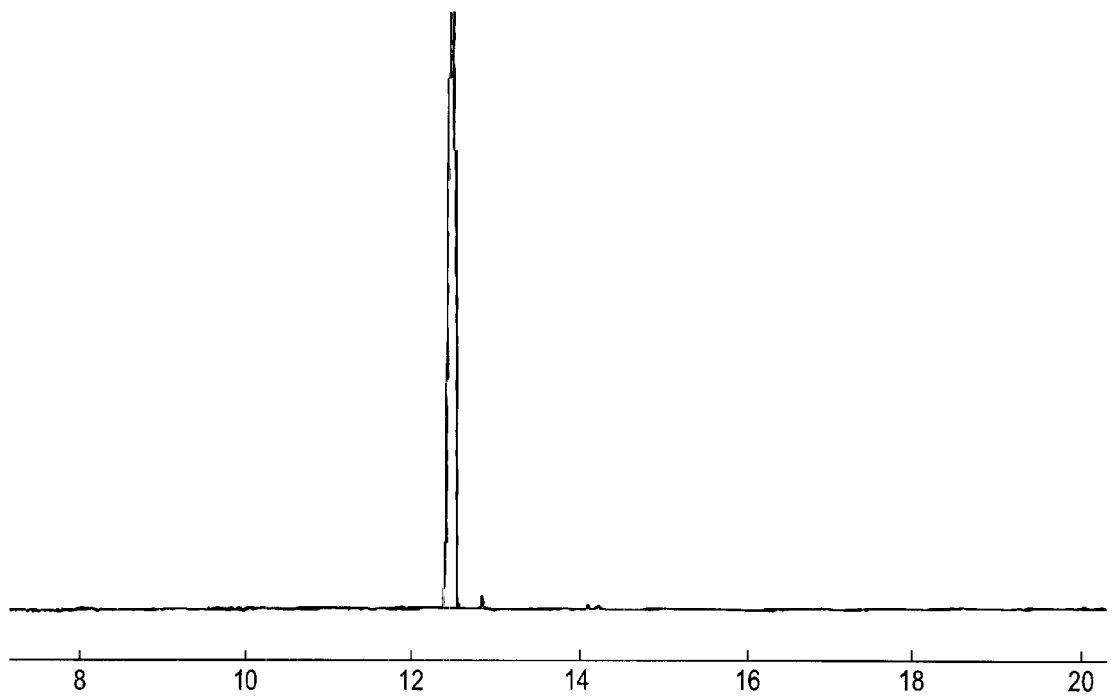
Fig. 3   Gas Chromatograme of 3,7-dimethyl, 5-one, 1-octene

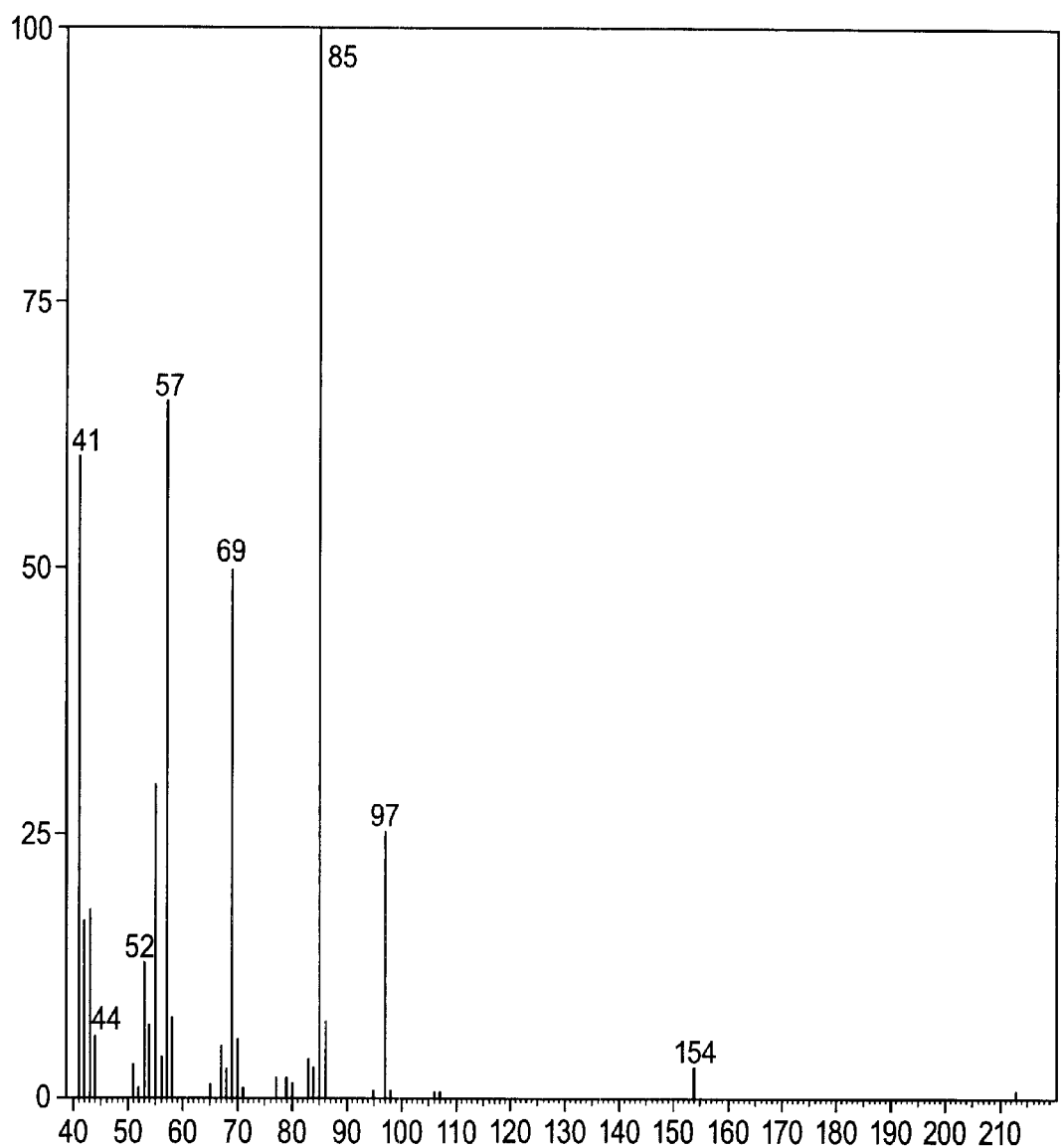
Fig. 4  Mass Spectrum of 3,7-dimethyl, 5-one, 1-octene

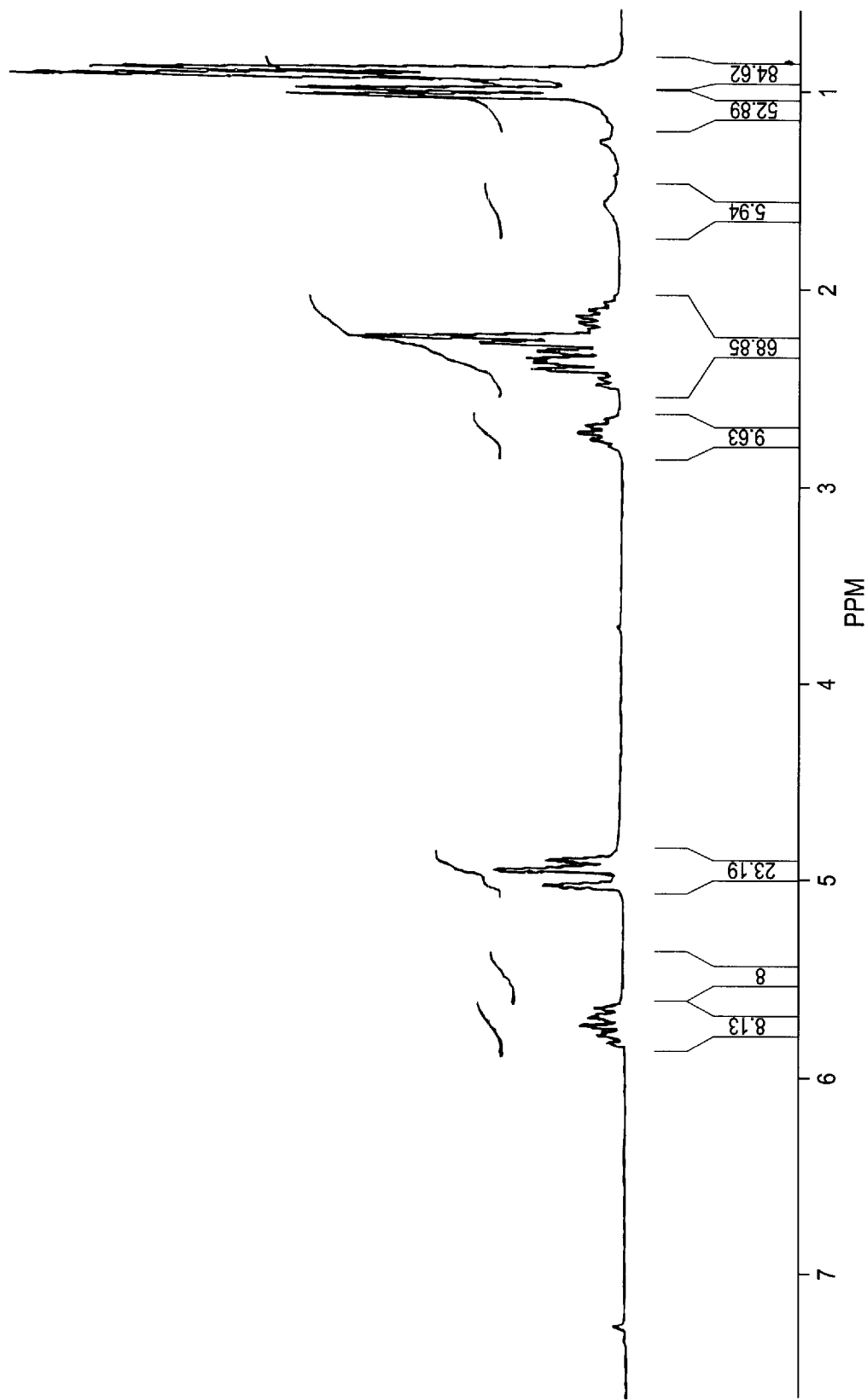
Fig. 5  $^1$H NMR of 3,7-dimethyl, 5-one, 1-octene

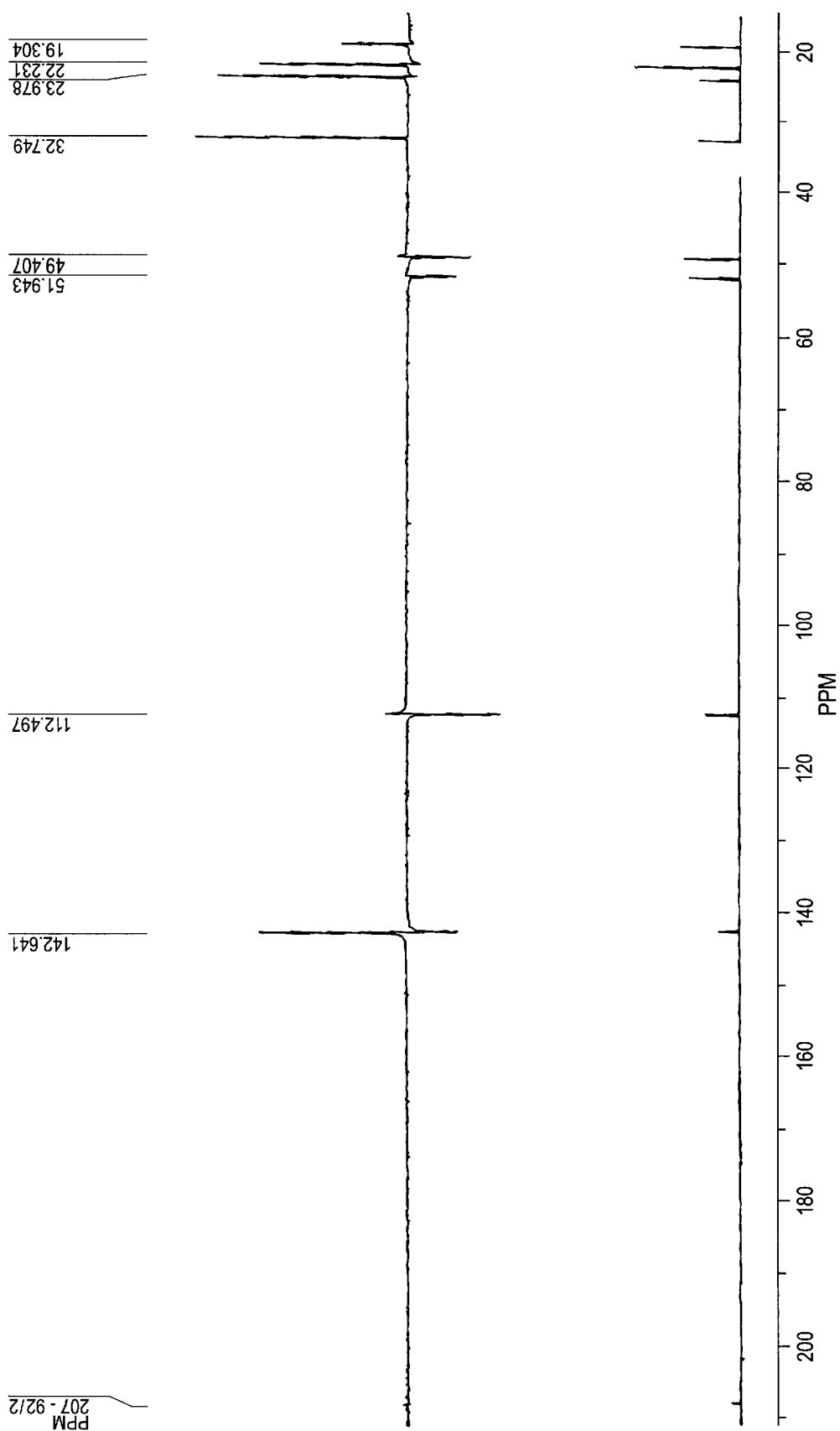
Fig. 6  $^{13}$C NMR of 3,7-dimethyl, 5-one, 1-octene

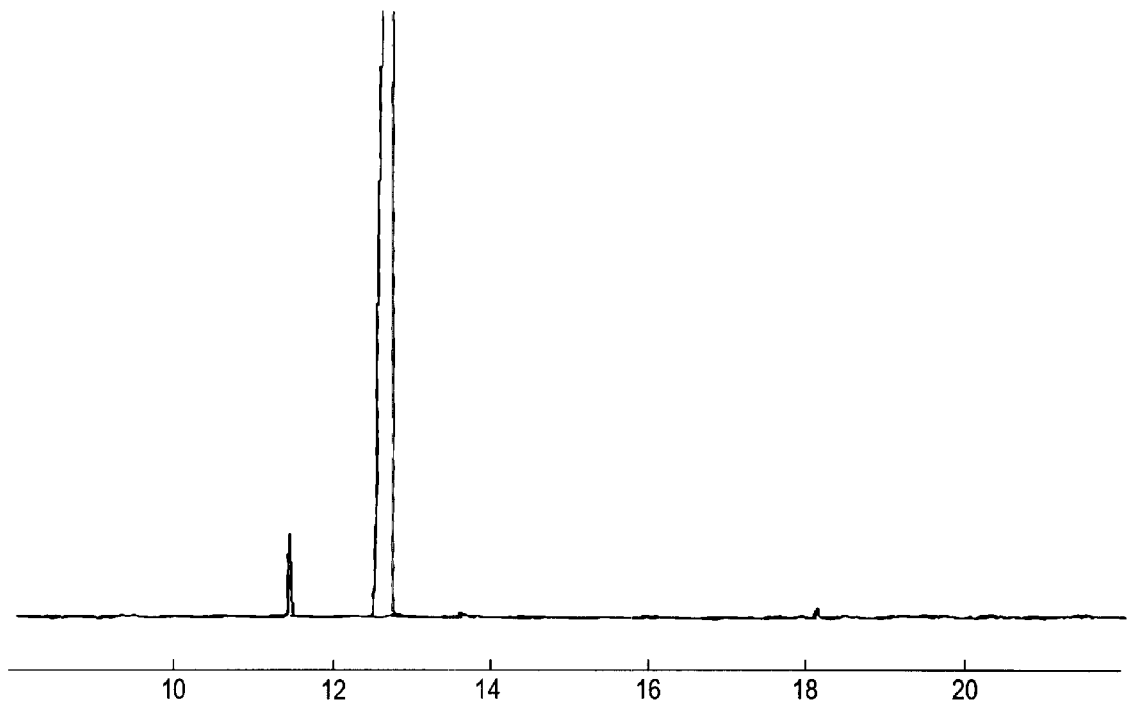
Fig. 7  Gas Chromatograme of 3,5,7 trimethyl 1-ene-5-octanol

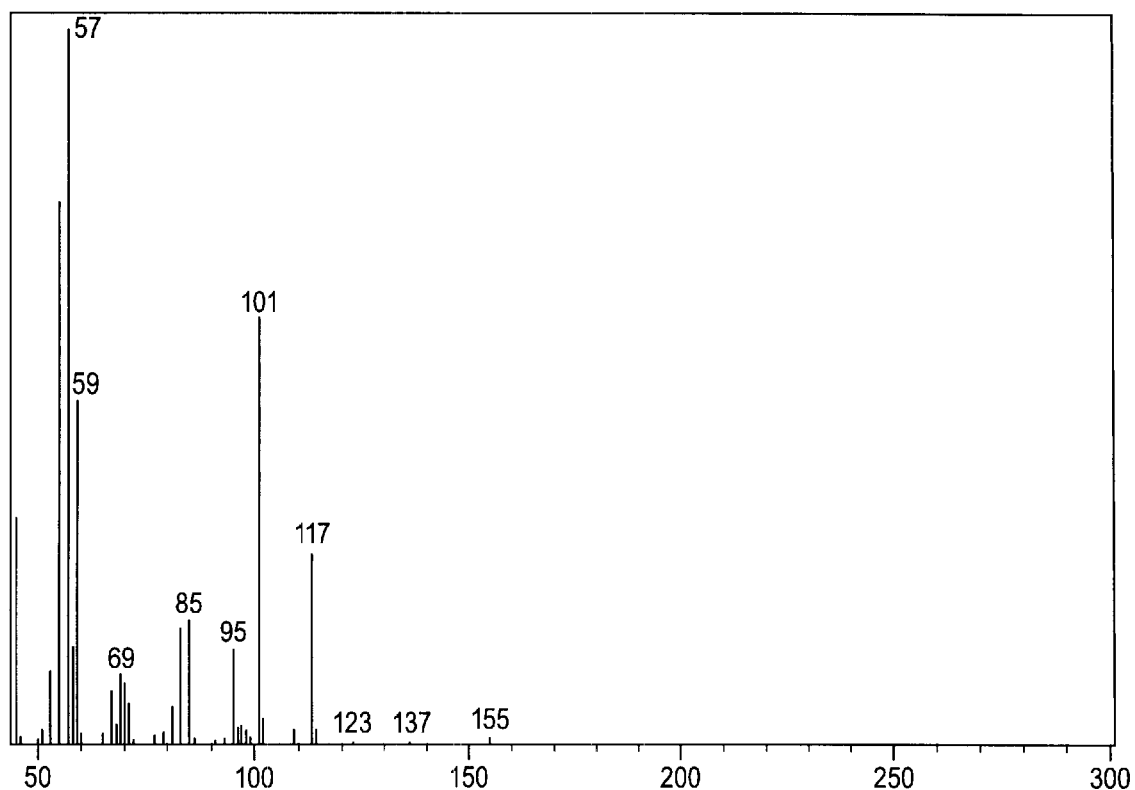
Fig. 8    Mass Spectrum of 3,5,7 trimethyl 1-ene-5-octanol

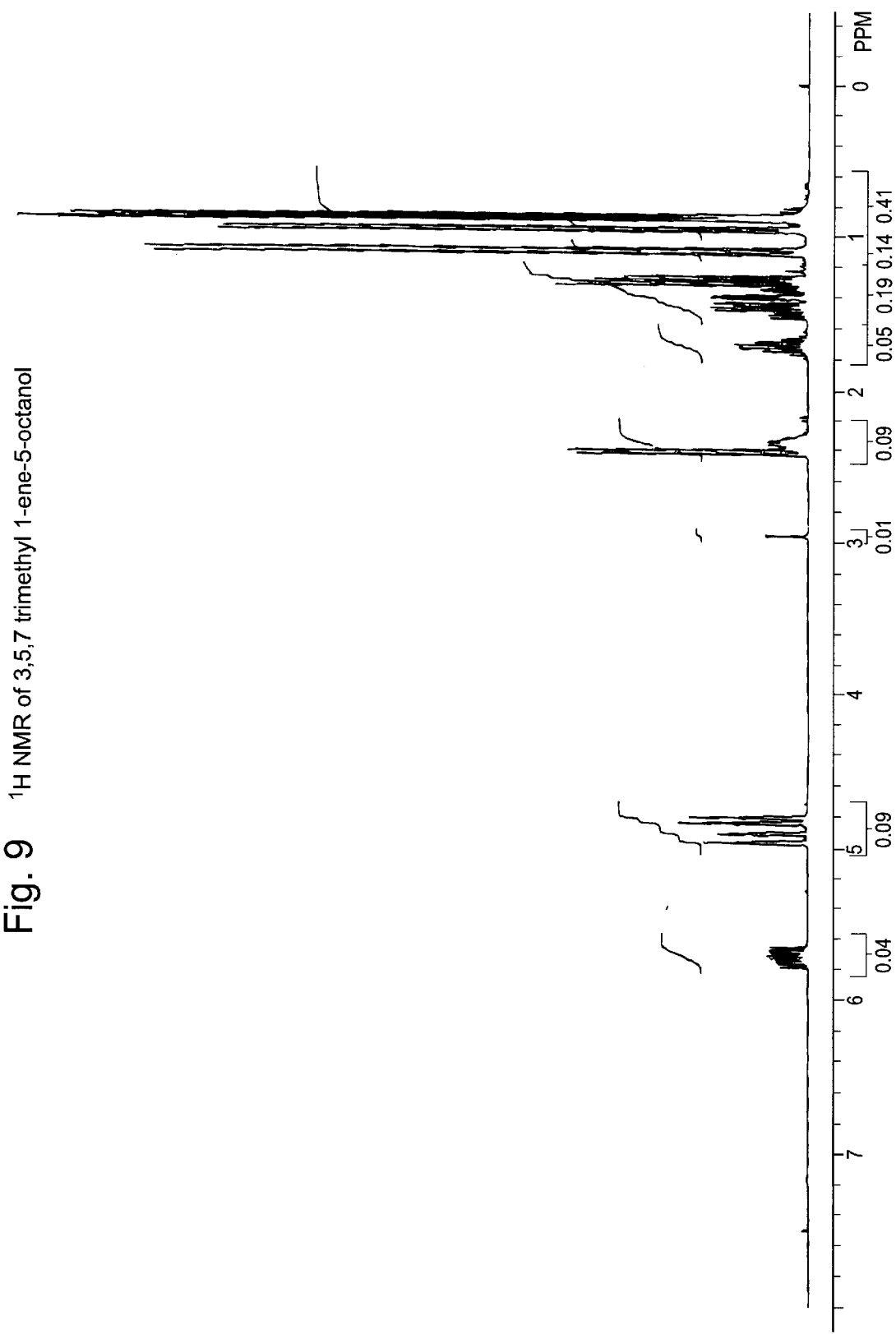
Fig. 9  ¹H NMR of 3,5,7 trimethyl 1-ene-5-octanol

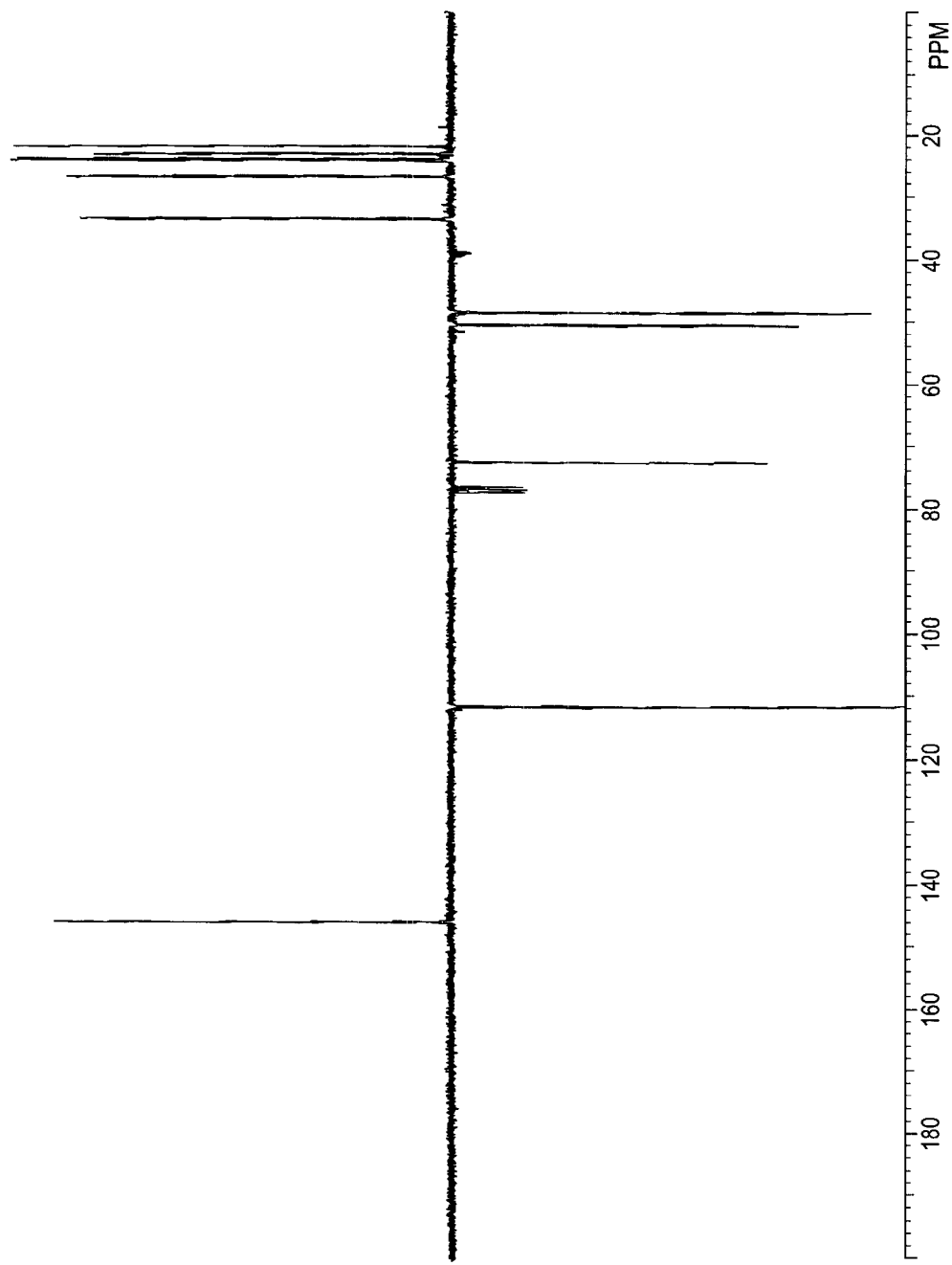
Fig. 10  $^{13}$C NMR of 3,5,7-trimethyl, 1-ene-5-octanol

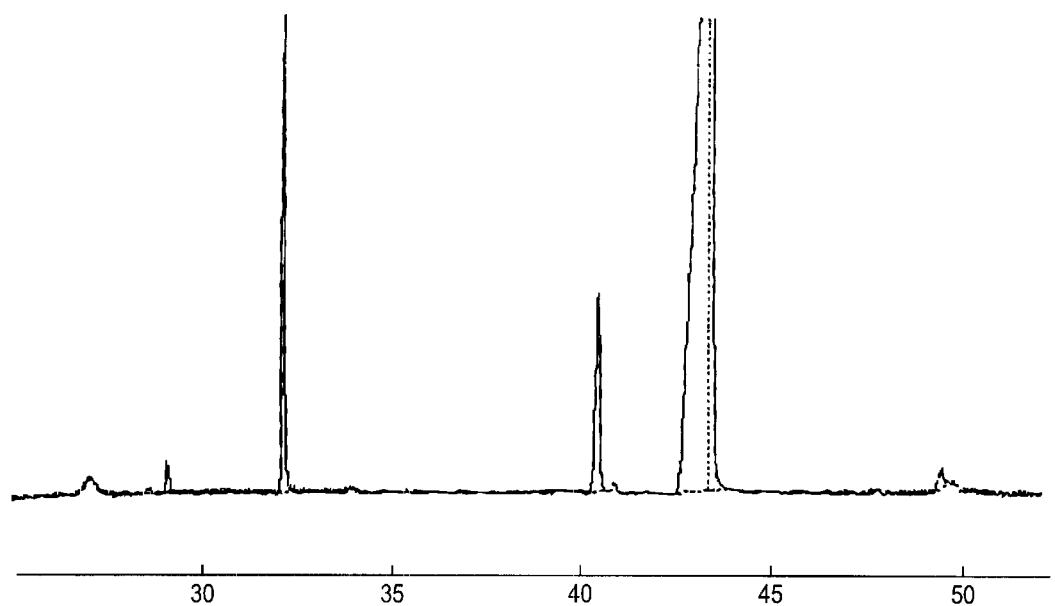
Fig. 11  Gas Chromatograme of 3,7-dimethyl, 5-benzyl, 1-ene-5-octanol

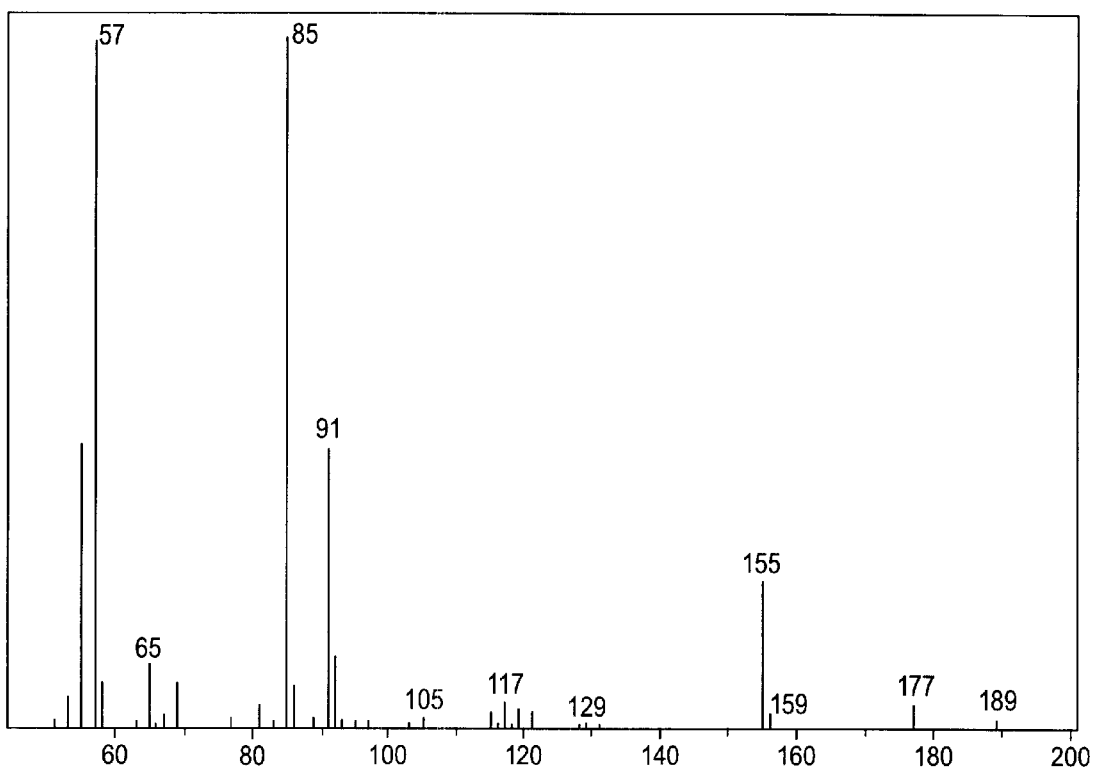
Fig. 12 Mass Spectrum of 3,7-dimethyl, 5-benzyl, 1-ene-5-octanol

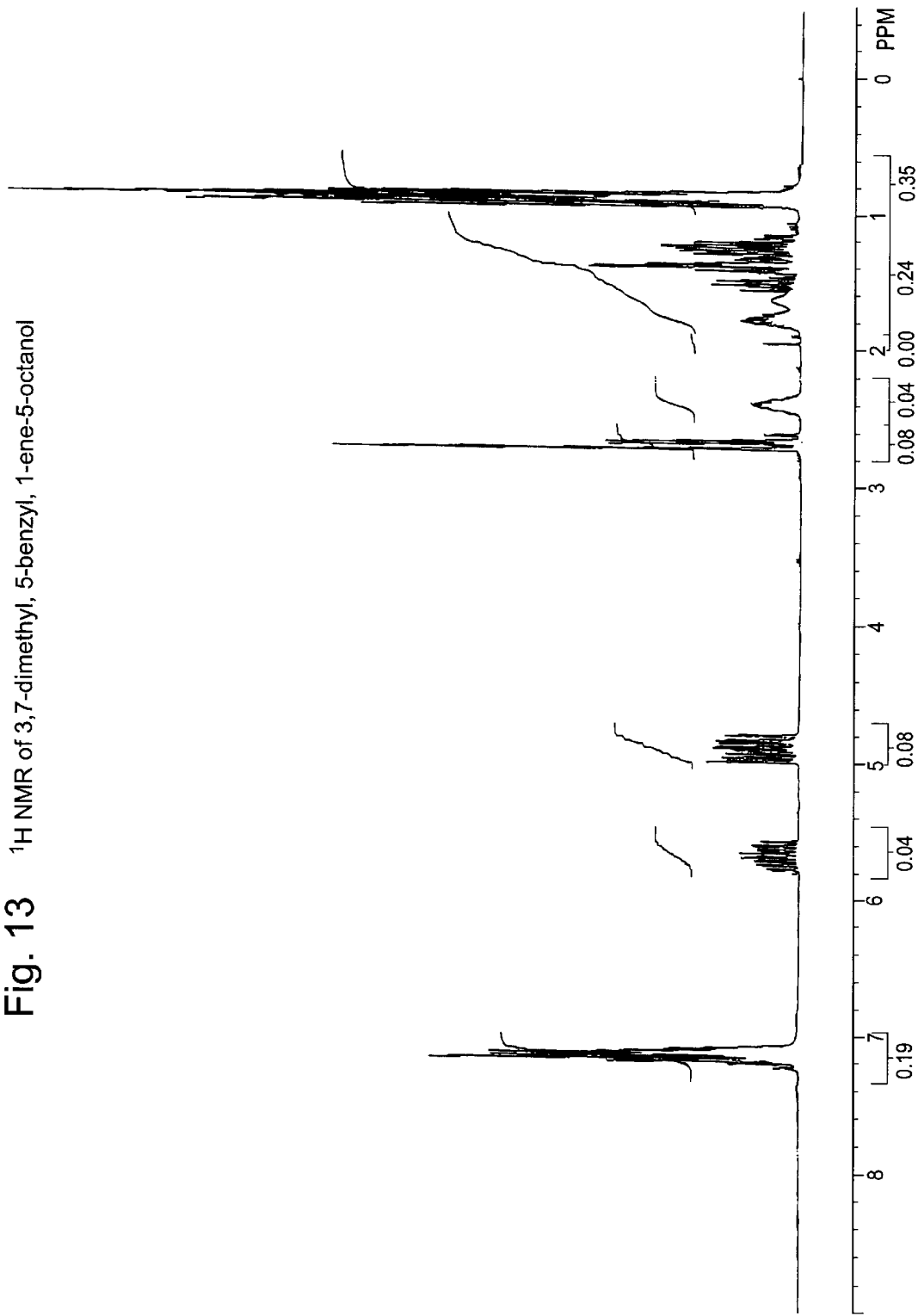
Fig. 13    ¹H NMR of 3,7-dimethyl, 5-benzyl, 1-ene-5-octanol

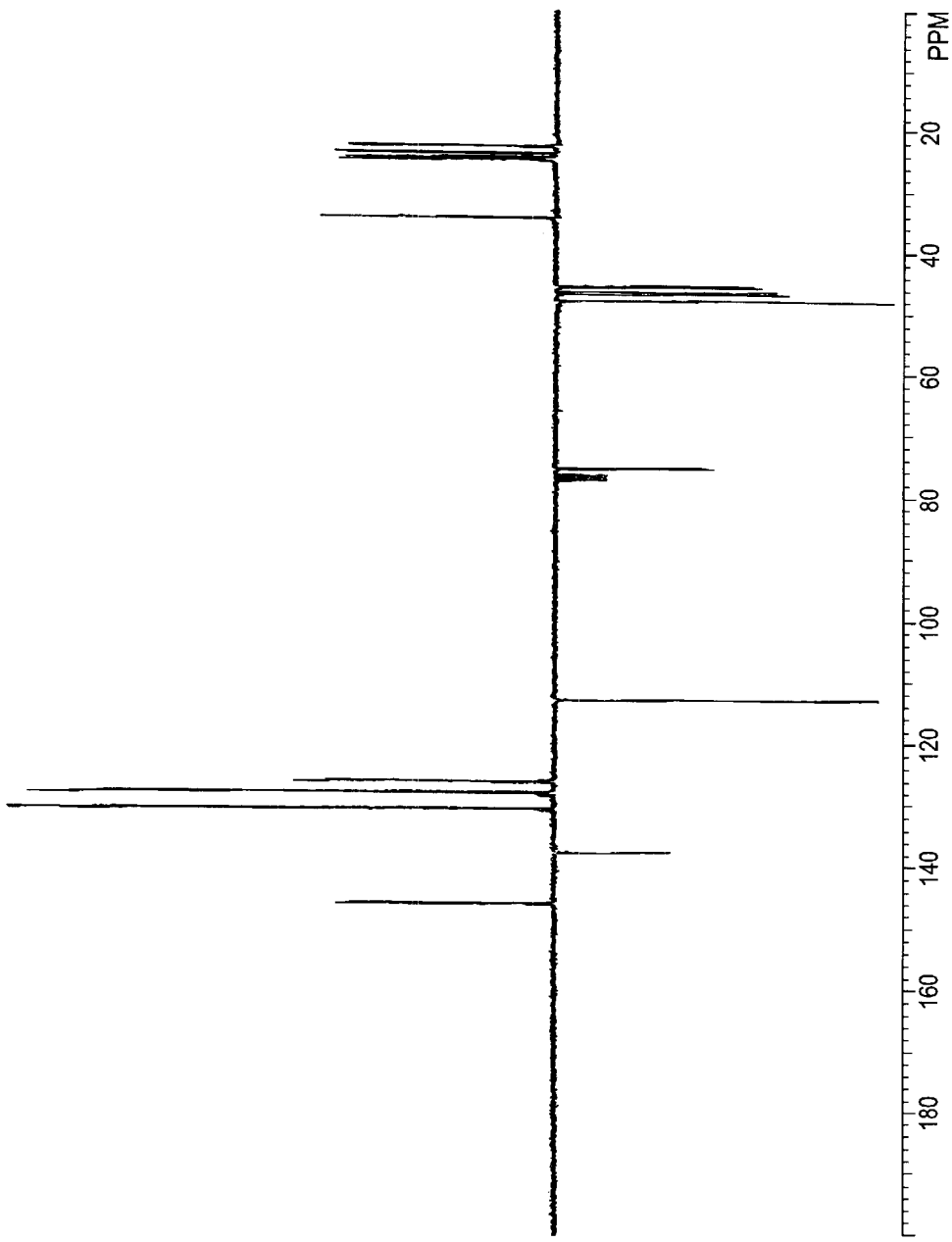
Fig. 14  $^{13}$C NMR of 3,7-dimethyl, 5-benzyl, 1-ene-5-octanol

DIHYDROTAGETONE ALCOHOL AND A METHOD FOR PREPARATION THEREOF FROM *TAGETES MINUTA* OIL

FIELD OF THE INVENTION

The present invention relates to a dihydrotagetone alcohol and to a method for the preparation thereof from from *Tagetes minuta* oil. More particularly the present invention relates to the preparation of dihydrotagetone methyl alcohol (3,5,7 trimethyl 1-ene, 5-octanol) and dihydrotagetone benzyl alcohol (3,7-dimethyl 5-benzyl, 1-ene, 5-octanol) by chemical transformation of dihydrotagetone present in essential oil of *Tagetes minuta*.

BACKGROUND OF THE INVENTION

Dihydrotagetone (3,7-dimethyl, 5-one, 1-octene) find application as perfumery and flavouring material. The synthesised molecules also find application as perfumery and flavour products or as an ingredient of perfumery and flavour products. Dihydrotagetone, dihydrotagetone methyl alcohol and dihydrotagetone benzyl alcohol are also useful in the pharmaceutical industry apart from the flavour and perfumery industries.

Derivatives of the above like acetates, epoxides, peroxides, acids, amides, halides, ethers and oximes etc. also result in products for perfumery, flavour and pharmaceutical industries.

Tagetes is a genus of herbs, commonly known as MARIGOLD, originally a native of Mexico and other warmer parts of America has now naturalised elsewhere in the tropics and sub-tropics. Several species have been introduced in India. Some of them are *Tagetes patula, Tagetes erecta, Tagetes minuta, Tagetes lucida* and *Tagetes tenuifolia*. The flower heads are used for garlands. Many Tagetes species yield strongly aromatic essential oils, all of which are known as Tagetes oil. The oil is obtained from the aerial parts of the plant by steam distillation or by extracting in petroleum- ether or benzene. Prolonged distillation spoils the aroma. The leaves, especially the tender ones and flower heads are rich in oil.

*Tagetes minuta*Linn. syn. *Tagetes glandulifera* Schrank (family- Compositae) is a highly aromatic annual, 1–2 m tall, native to South America, has naturalised near the waste places and on dry embankments in the North-West Himalayas between altitudes of 1250 and 2500 m.

Among all the Tagetes species grown in India, *Tagetes minuta* appears to give the highest yield of the essential oil with maximum carbonyl content, calculated as tagetone. Reference may be made to Villeirs F. J., Garbers C. F and Lasnvie R. N., 1971, synthesis of Tagetones and their occurrence in oil of *Tagetes minuta, Phytochemistry*, 10, 1359. Reference may also be made to Lawrence B. M., 1992, progress in essential oils, *Perf & Flav*, 17, 131–132. Another reference may be made to Singh B., Sood R. P and Singh V. 1992, chemical composition of Tagetes minuta L. from Himachal Pradesh (India), *J., Essent. Oil Res.* 4, 525.

OBJECTS OF THE INVENTION

The main object of the present invention is the chemical modification of dihydrotagetone into two new perfumery and flavouring molecules.

Another object of the present invention is to provide easy and convenient method for enrichment of monoterpene and ketones in *Tagetes minuta* oil by solvent-solvent partitioning.

Still another object of the present invention is to provide methodology for isolation of dihydrotagetone (3,7-dimethyl, 5-one, 1-octene) in 100% purity having characteristic fresh, sweet, fruity and flowery odour.

Another object of the present invention is to provide a starting material for synthesis of a new perfumery and flavour molecule (3,5,7 trimethyl 1-ene, 5-octanol) in 99% yield, having minty, spicy, fresh and fruity odour.

Yet another object of the present invention is to provide starting material for synthesis of a new perfumery and flavour molecule (3,7-dimethyl 5-benzyl, 1-ene, 5-octanol) in 75% yield with sweet, flowery, aromatic like odour.

BRIEF DESCRIPTION OF THE ACCOMPANYING DRAWINGS

FIG. 1 represents a gas chromatogram of *Tagetes minuta* oil.

FIG. 2 is a gas chromatogram of 3,7-dimethyl, 5-one, 1-octene rich fraction.

FIG. 3 is a gas chromatogram of 3,7-dimethyl, 5-one, 1-octene.

FIG. 4 is a mass spectrum reading of 3,7-dimethyl, 5-one, 1-octene.

FIG. 5 is $^1$H NMR of 3,7-dimethyl, 5-one, 1-octene.

FIG. 6 is $^{13}$C NMR of 3,7-dimethyl, 5-one, 1-octene.

FIG. 7 is a gas chromatogram of 3,5,7-trimethyl 1-ene-5-octanol.

FIG. 8 is a mass spectrum reading of 3,5,7-trimethyl 1-ene-5-octanol.

FIG. 9 is $^1$H NMR of 3,5,7-trimethyl 1-ene-5-octanol.

FIG. 10 is $^{13}$C NMR of 3,5,7-trimethyl 1-ene-5-octanol.

FIG. 11 is gas chromatogram of 3,7-dimethyl, 5-benzyl, 1-ene-5-octanol.

FIG. 12 is a mass spectrum reading of 3,7-dimethyl, 5-benzyl, 1-ene-5-octanol.

FIG. 13 is $^1$H NMR of 3,7-dimethyl, 5-benzyl, 1-ene-5-octanol.

FIG. 14 is $^{13}$C NMR of 3,7-dimethyl, 5-benzyl, 1-ene-5-octanol.

SUMMARY OF THE INVENTION

Accordingly, the present invention relates to a dihydrotagetone alcohol of the general formula 1, wherein R is an alkyl or aryl group.

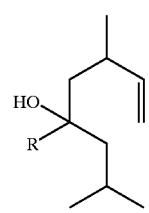

Formula 1

The present invention also relates to a process for preparation of a dihydrotagetone alcohol of general formula 1

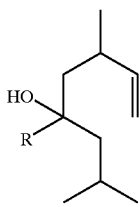

Formula 1 from *Tagetes minuta* oil, said process comprising
i) solvent-solvent partitioning of *Tagetes minuta* oil
ii) evaporating solvent and isolating dihydrotagetone
iii) reacting the dihydrotagetone so isolated in step (ii) above with a Grignard reagent
iv) extracting the resultant mixture of step (iii) with a polar solvent, and
v) evaporating and drying the solvent to obtain the desired product.

In one embodiment of the invention, the solvent for partitioning is selected from the group consisting of n-pentane, n-hexane, n-heptane and acetonitrile.

In another embodiment of the invention, dihydrotagetone is converted into dihydrotagetone alcohols with a yield ranging from 75%–99%.

In a further embodiment of the invention, the dihydrotagetone alcohols formed are dihydrotagetone methyl alcohol (3,5,7-trimethyl, 1-ene, 5-octanol), dihydrotagetone benzyl alcohol (3,7-dimethyl, 5-benzyl, 1-ene, 5-octanol) and other dihydrotagetone alcohol derivatives selected from ethyl, butyl, propyl, and phenyl alcohols.

In another embodiment of present invention *Tagetes minuta* oil was obtained by hydro -steam distillation in laboratory/pilot scale.

In yet another embodiment of present invention, dihydrotagetone (3,7-dimethyl, 5-one, 1-octene) is converted to 3,5,7 trimethyl 1-ene-5-octanol and 3,7-dimethyl, 5-benzyl, 1-ene-5-octanol by Grignard reaction, comprising first preparing Grignard reagent using magnesium turnings in diethyl ether and dropwise addition of alkyl or aryl halide at 0° C. with continues stirring on magnetic stirrer, adding dihydrotagetone to the above prepared Grignard reagent dropwise with continues stirring.

DETAILED DESCRIPTION OF THE INVENTION

Dihydrotagetone and two other molecules synthesised from it were evaluated for their odour profiles.

Dihydrotagetone is converted to alkyl and aryl alcohols by easy, convenient and in good yields. These alcohols could not be prepared by alkyl and aryllithium and alkyzinc reagents but in low yields. Lithium dimethyl copper reacts with aldehyde and ketones to give expected alcohols. Aromatic aldehydes and ketones can be alkylated and reduced in one reaction vessel by treatment with an alkyl and aryllithium. The reference may be made to Furakawa and Kawabata, Adv. Organomet. Chem. 12 103–121, 1974. The other reference may be made to House, Prabhu, Wilkins and Lee, J. Org. Chem., 41, 3067, 1976. Yet another reference may be made to Hall & Lipsky, J. Org. Chem., 38, 1735, 1973.

*Tagetes minuta* plant grown in the farms of the Institute of Himalayan Bioresource Technology was subjected to hydrodistillation/hydrosteam distillation on pilot plant for four to five hours. After the distillation is completed, the oil is separated and dried over anhydrous sodium sulphate and then kept in amber colored bottles without leaving any air gap. After that, the oil was subjected to fractionation through solvent—solvent extraction with n-pentane (n-hexane may be taken in place of n-pentane) and acetonitrile for enrichment of monoterpene and ketones and solvent evaporation. The acetonitrile fraction was subjected to the column chromatography on silica gel and eluted initially with n-hexane and then increased order of polarity with ethyl acetate upto 2%. Dihydrotagetone got eluted with 2% ethyl acetate.

Synthesis of Dihydrotagetone Methyl Alcohol

The Grignard reagent was prepared with methyl iodide and magnesium in dry ether and iodine was used as a catalyst to start the reaction. Then dihydrotagetone was added drop-wise to this with continuous stirring at 0° C. for two hours. The reaction was monitored on TLC and the final purity of the product was confirmed by GC, GC-MS, IR, $^1$H & $^{13}$C NMR.

Synthesis of Dihydrotagetone Benzyl Alcohol

The Grignard reagent was prepared with benzyl chloride and magnesium in dry ether and iodine was used as a catalyst to initiate the reaction. To this Dihydrotagetone was added drop-wise with continuous stirring at 0° C. for two hours. The reaction was monitored on TLC and the final purity of the product was confirmed by GC, GC-MS, IR, $^1$H & $^{13}$C NMR.

A comparative statement of Tagetes oil and its components have been made with respect to the different characteristic. Tagetes oil It is reddish yellow mobile and clear liquid which has a powerful pungent low reminiscent of rancid butter, spearmint and in great dilutions of apples. The oil is reported to have Specific gravity 0.8405–0.8457, refractive index 1.4809–1.4905, optical rotation +2–+1° at 27° C.

On exposure to air and light, the oil has tendency to polymerize and become an almost solid gel.

Ocimene (3,7-dimethyl-1,3,6 octatriene)

It is colorless or very pale straw colour mobile liquid with sp. 0.80 and boiling point 177° C. It is insoluble in water and soluble in alcohol. It polymerizes quickly when exposed to air oxygen. It is warm-herbaceous, very diffusive odour of poor tenacity. The sweetness is almost floral and there is immediate similarity to neroli oil.

Cis-tagetone (3,7-dimethyl, 5-one, 1,3-octdiene)

Light greenish yellow coloured liquid with molecular formula $C_{10}H_{16}O_2$ molecular wt. 152, boiling point 205–210° C., d15–5, 0–88 $n_b^2$ 1.48. The compound is highly unstable and polymerize in presence of air and light.

trans-tagetone (3,7-dimethyl, 5-one, 1,3-octdiene)

Light coloured yellowish green with molecular formula $C_{10}H_{16}O_2$ molecular wt. 152, boiling point 44–45° C./0.1 mm $n_b^2$1.488.

Cis- and Trans Ocimenone (3,7-dimethyl, 5-one, 1, 3,6-octtriene)

These are highly unsaturated acyclic monoterpene lactones and tend to polymerise at very faster rate. No other data is available for these compounds.

Dihydrotagetone (3,7-dimethyl, 5-one, 1-octene)

It is colourless liquid with fresh sweet fruity, light Tagetes, flowery and green odour with molecular wt. 154 and formula $C_{10}H_{16}O$, Red index. 1.434. Dihydrotagetone only the major stable compound in *Tagetes minuta* oil and does not participate in polymerization of oil. In polymerized oil dihydrotagetone is the major component.

Dihydrotagetone methyl alcohol (3,5,7-trimethyl 1-ene 5-octanol)

It is colourless liquid with minty, spicy, fresh fruity fragrance. Its molecular weight is 170 and molecular formula is $C_{11}H_{22}O$. Ref. Index 1.448. It is stable compound and does not polymerize like Tagetes oil.

Dihydrotagetone benzyl alcohol (3,7-dimethyl, 5-benzyl, 1-ene5-octanol)

It is light yellow liquid with sweet, flowery, aromatic having molecular weight 246 and formula $C_{17}H_{25}O$. It refractive index is 1.485.

The following examples are given by way of illustration and therefore should not be construed to limit the scope of the present invention.

EXAMPLE 1

In 350 ml of *Tagetes minuta* oil, 250 ml of acetonitrile and 250 ml of n-pentane were added and mixture was shaken slowly in separating funnel. This was allowed to stand for half an hour. After separating two layers, the acetonitrile layer was washed three times with n-pentane (250 ml each), the pentane fractions were combined and the solvent evaporated i.e. n-pentane from pentane fraction & acetonitrile from acetonitrile fraction. After analysing both the fractions by Gas Chromatographic technique, following percentages of ocimene (hydrocarbon) and dihydrotagetone (ketone) were observed. The freshly distilled *Tagetes minuta* oil contained ocimene 54.97%, and dihydrotagetone 32.58%.
1. Pentane fraction: Ocimene 62.5%, Dihydrotagetone 24.62%.
2. Acetonitrile fraction: Ocimene 26.96%, Dihydrotagetone 69.87%.

The enrichment of Dihydrotagetone was achieved from 32.5%, present in freshly distilled oil to nearly 70% after partitioning.

The acetonitrile fraction was subjected to the column chromatography on Silica gel (60–120 mesh), run initially with n-hexane and then with an increasing order of polarity with ethyl acetate upto 2% to get pure dihydrotagetone. Confirmation of dihydrotagetone was made by various analytical techniques like—IR, GC, GC-MS, $^1H$ & $^{13}C$ NMR spectroscopy and the odour profile was checked.

Dihydrotagetone (3,7-dimethyl, 5-one, 1-octene)

Odour: Fresh, sweet, fruity, flowery ,light tagetes like and green.

Molecular Formula: $C_{10}H_{18}O$ m/e(%): 154 (10), 97 (30), 85 (100), 69 (50), 57 (65), 55 (35), 53 (18), 44 (15), 41 (60)

$^1H$-NMR (ppm, $CDCl_3$): 4.89–5.02 (2H, m, H-1), 5.64–5.78 (1H, m, H-2), 2.68–2.75 (1H, m, H-3), 2.09–2.47 (4H, m, H-4,6), 1.11–1.26 (3H, d, J=6 Hz, H-8), 1.02–0.89 (6H, d, J=6 Hz, H-9, 10).

$^{13}C$-NMR(ppm, $CDCl_3$): 112.49 (C-1), 142.64 (C-2), 23.97 (C-3), 207.9 (C-4), 51.94 (C-4), 49.4 (C-6), 32.75 (C-7), 22.23 (C-8), 19.8 (C-9), 22.23 (C-10).

EXAMPLE 2

Magnesium turnings (4.00 gm) in diethylether (50 ml) in 500 ml round bottom flask were stirred with the help of magnetic bead. Methyl iodide (22.0 ml) in diethyl ether (110 ml) was mixed drop—wise to above solution with continuous stirring at low temperature (0° C.). Few crystals of iodine were added to catalyse the reaction. Solution was stirred till whole of magnesium dissolved.

To the above-prepared Grignard reagent, dihydrotagetone (16 ml) in 90 ml of diethylether was added drop—wise and stirring was continued for two hours. The reaction mixture was poured in the cold saturated solution of ammonium chloride and the organic layer was extracted with diethyl ether. The diethylether layer was washed four times with water (100 ml each), dried over anhydrous sodium sulphate and ether was evaporated in rotavapor. The percentage yield of reaction product was 99% as confirmed by Gas Chromatography. The final structure was elucidated by GC/MS, Ir, $^1H$- & $^{13}C$-NMR spectroscopy as 3,5,7 trimethyl 1-ene-5-octanol. The odour evaluation was carried out at DRAGCO Company, Vienna by internationally renowned perfumerists and flavourists.

Dihydrotagetone methyl alcohol (3,5,7 trimethyl 1-ene-5-octanol)

Odour: minty, spicy, fresh fruity

Molecular Formula: $C_{11}H_{22}O$ m/e(%): 155(2.5), 137(5), 113(50), 109(15), 101(95), 95(52.5), 85(17.5), 69(17), 57(45), 55(72), 43(100).

$^1H$-NMR (ppm, $CDCl_3$): 0.86 (3H, d, J=5.5 Hz, H-8), 0.88 (3H, d, J=5.5Hz, H-9), 0.95 (3H, d, J=7.0 Hz, H-10), 1.10 (3H, J=8.5 Hz, H-11), 1.26–1.33 (2H, m, H-4), 1.41–1.51(2H, m, H-6), 1.68–1.75 (1H, m, H-7), 2.39–2.42 (1H, m, H-3), 4.79–4.96 (2H, m, H-1), 5.01–5.73 (1H, m, H-2).

$^{13}C$-NMR (ppm, $CDCl_3$): 111.73 (C-1), 145.68 (C-2), 24.12 (C-3), 48.59 (C-4) 72.55 (C-5), 50.59 (C-6), 24.31 (C-7), 22.07 (C-8), 23.36 (C-9), 26.92 (C-10), 33.75 (C-11).

EXAMPLE 3

Magnesium turnings (5.52 gm) in diethylether (80 ml) in 500 ml round bottom flask were stirred with the help of magnetic bead. Benzyl chloride (28.79 gm) in diethyl ether (120 ml) was mixed drop—wise to above solution with continuous stirring at low temperature (0° C). Few crystals of iodine were mixed to catalyse the reaction. Solution was stirred till whole of magnesium dissolved.

To the above-prepared Grignard reagent, dihydrotagetone (21.5 ml) in 130 ml of diethylether was added drop by drop and stirring was continued for two hours. The reaction mixture was poured in the saturated solution of ammonium chloride and the organic layer was extracted with diethyl ether. The diethylether layer was washed with water for four times (100 ml each), dried over anhydrous sodium sulphate and ether was evaporated in rotavapor. The product yield was 75% and confirmed with the help of Gas Chromatography. The final structure was elucidated by GC, GC/MS, IR, $^1H$-NMR & $^{13}C$-NMR spectroscopy as 3,7-dimethyl 5-benzyl, 1-ene, 5-octanol. The odour value was carried out at DRAGCO Company Vienna by internationally renowned perfumerists and flavourists.

Dihydrotagetone benzyl alcohol (3,7-dimethyl, 5-benzyl, 1-ene-5-octanol)

Odour: sweet, flowery, aromatic like Molecular Formula: $C_{17}H_{26}O$ m/e(%): 229(1), 228(5), 199(3.5), 185(8.5), 173 (13), 155(32), 137(17), 117(82), 91(100), 85(55), 81(32), 57(24.5), 43(10).

¹H-NMR (ppm, CDCl₃): 0.86 (3H, d, J=6.5 Hz, H–8), 0.89 (3H, d, J=6.5Hz, H–10), 0.92 (3H, d, J=6.5Hz, H–9), 1.15–1.81 (5H, m, H–4,6,7), 2.38 (₁H, m, H–3), 2.66–2.71 (2H, m, H–11), 4.78–4.97 (2H, m, H–1), 5.57–5.75(1H, m, H–2), 7.07–7.19 (5H, m, H-phenyl).

¹³C-NMR (ppm, CDCl₃): 112.9 (C–1), 146.1 (C–2), 24.8 (C–3), 47.9 (C–4), 75.5 (C–5), 45.6 (C–6), 24.5 (C–7), 23.9 (C–8), 23.7 (C–9), 22.7 (C–10), 45.5 (C–11), 137.6 (C–1'), 130.6 (C–2'), 0127.8 (C–3'), 126.1 (C–4'), 127.8 (C–5'), 130.6 (C–6').

The possible reaction schemes for the synthesis of the novel dihydrotagetone alcohol of the invention are given below:

A route for the synthesis of 3,5,7 trimethyl 1-ene-5-octanol from 3,7-dimethyl, 5-one, 1-octene.

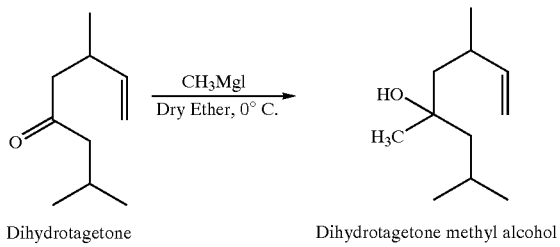

Dihydrotagetone     Dihydrotagetone methyl alcohol

A route for the synthesis of 3,7-dimethyl, 5-benzyl, 1-ene5-octanol from 3,7-dimethyl, 5-one, 1-octene

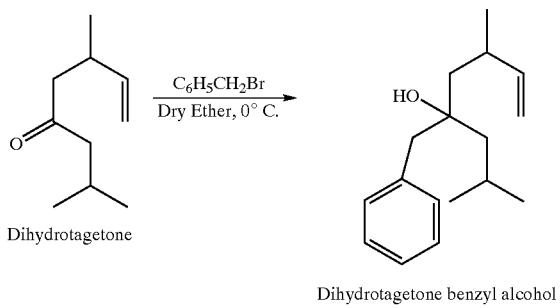

Dihydrotagetone

Dihydrotagetone benzyl alcohol

The Main Advantages of Present Invention are
1. Enrichment of dihydrotagetone (3,7-dimethyl, 5-one, 1-octene) a constituent of *Tagetes minuta* oil by solvent—solvent partitioning using n-pentane and acetonitrile.
2. Isolation and identification of dihydrotagetone (3,7-dimethyl, 5-one, 1-octene) a constituent of *Tagetes minuta* oil as a new perfumery and flavouring material having fresh, sweet, fruity flowery, light tagetes and green.
3. Use of dihydrotagetone (3,7-dimethyl, 5-one, 1-octene) as a starting material for the development of two new aroma molecules.
4. Chemical transformation of dihydrotagetone (3,7-dimethyl, 5-one, 1-octene) into its dihydrotagetone methyl alcohol (3,5,7-trimethyl, 1-ene-5-octanol) derivative in 99% yield with minty, spicy and fresh fruity aroma note.
5. Chemical transformation of dihydrotagetone (3,7-dimethyl, 5-one, 1-octene) into its dihydrotagetone benzyl alcohol (3,7-dimethyl, 5-benzyl,1-ene-5-octanol) 75% yield with sweet, flowery and aromatic aroma note.
6. The new aroma molecules useful in perfumery flavouring and pharmaceutical industry can be prepared cost effectively by easy and convenient process from dihydrotagetone.

We claim:

1. Dihydrotagetone alcohol of the general formula 1, wherein R is an alkyl or aryl group.

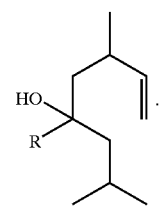

Formula I

2. A process for preparation of a dihydrotagetone alcohol of the general formula 1

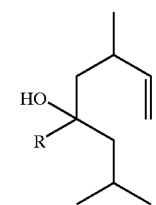

Formula 1 from *Tagetes minuta* oil, said process comprising
  i) solvent-solvent partitioning of *Tagetes minuta* oil
  ii) evaporating solvent and isolating dihydrotagetone
  iii) reacting the dihydrotagetone so isolated in step (ii) above with a Grignard reagent
  iv) extracting the resultant mixture of step (iii) with a polar solvent, and
  v) evaporating and drying the solvent to obtain the desired product.

3. A process as claimed in claim 2 wherein the solvent for partitioning is selected from the group consisting of n-pentane, n-hexane, n-heptane and acetonitrile.

4. A process as claimed in claim 2 wherein dihydrotagetone is converted into dihydrotagetone alcohols with a yield ranging from 75%–99%.

5. A process as claimed in claim 2 wherein dihydrotagetone alcohols formed are dihydrotagetone methyl alcohol (3,5,7-trimethyl, 1-ene, 5-octanol), dihydrotagetone benzyl alcohol (3,7-dimethyl, 5-benzyl, 1-ene, 5-octanol) and other dihydrotagetone alcohol derivatives selected from ethyl, butyl, propyl, and phenyl alcohols.

\* \* \* \* \*